(12) United States Patent
Sohn et al.

(10) Patent No.: US 8,688,195 B2
(45) Date of Patent: Apr. 1, 2014

(54) FLUORESCENT INDICATION CLIP FOR SURGERY

(75) Inventors: Dae-Kyung Sohn, Gyeonggi-do (KR); Kwang-Gi Kim, Gyeonggi-do (KR); Yong-Doo Choi, Dongan-gu (KR); Kyoung-Won Nam, Gyeonggi-do (KR); Hyun-Ho Kim, Seoul (KR)

(73) Assignee: National Cancer Center (KR)

( * ) Notice: Subject to any disclaimer, the term of this patent is extended or adjusted under 35 U.S.C. 154(b) by 564 days.

(21) Appl. No.: 12/612,305

(22) Filed: Nov. 4, 2009

(65) Prior Publication Data

US 2010/0331674 A1 Dec. 30, 2010

(30) Foreign Application Priority Data

Jun. 29, 2009 (KR) .................................. 2009-58067

(51) Int. Cl.
*A61B 5/05* (2006.01)

(52) U.S. Cl.
USPC .......................................... 600/424; 600/426

(58) Field of Classification Search
USPC .......................................... 600/426; 606/151
See application file for complete search history.

(56) References Cited

U.S. PATENT DOCUMENTS

| | | | |
|---|---|---|---|
| 5,772,593 | A | 6/1998 | Hakamata |
| 7,357,805 | B2 | 4/2008 | Masuda et al. |
| 2002/0029032 | A1* | 3/2002 | Arkin .................................. 606/1 |
| 2005/0182318 | A1* | 8/2005 | Kaji et al. ....................... 600/424 |
| 2006/0259049 | A1 | 11/2006 | Harada et al. |

FOREIGN PATENT DOCUMENTS

| | | |
|---|---|---|
| JP | 1997-024053 B2 | 1/1997 |
| KR | 10-2005-0110013 | 11/2005 |
| KR | 10-2005-0110013 A | 11/2005 |

OTHER PUBLICATIONS

Rena Lee, Ph.D. et al., "Analysis of the Movement of Surgical Clips Implanted in Tumor Bed during Normal Breast Cancer Patients," The Korean Society for Therapeutic Radiology & Oncology, 24(3), pp. 192-200 (Jul. 2006).

* cited by examiner

*Primary Examiner* — Parikha Mehta
(74) *Attorney, Agent, or Firm* — Foley & Lardner LLP; Michel Morency

(57) ABSTRACT

Provided is a fluorescent indication clip for surgery that has an improved function as a position indicator due to a photoreactive fluorescent material included in the bio-clip, and allows people to rapidly and easily detect the accurate position of an internal operation region, and thus can improve operation accuracy and reduce side effects caused by excessive incision. The fluorescent indication clip includes a self-spreadable clip body, a fluorescent indicator prepared at the rear end of the clip body and including a photo-reactive fluorescent material, and a clamper configured to slide from a position at which the clamper is mounted on the fluorescent indicator to the clip body by an external force, and fasten the clip body to narrow front ends of the clip body.

8 Claims, 10 Drawing Sheets

FLUORESCENT INDICATION CLIP FOR SURGERY

CROSS-REFERENCE TO RELATED APPLICATION

This application claims priority to and the benefit of Korean Patent Application No. 2009-0058067, filed Jun. 29, 2009, the disclosure of which is incorporated herein by reference in its entirety.

FIELD OF THE INVENTION

The present invention relates to a fluorescent indication clip for surgery, and more particularly, to a fluorescent indication clip for surgery, which reinforces a function as a position indicator by mounting a photo-reactive fluorescent material on the bio-clip and thus allows a surgeon to rapidly and easily detect an accurate position of an internal operation region.

BACKGROUND

Typical surgical operations used to treat colon cancer, stomach cancer, etc., are performed by inserting an endoscope into a body, visually checking an operation region, for example, a cancer region, and then incising and removing the cancer region inside the body through abdominal or laparoscopic surgery.

In these surgical operations, however, a visual angle and range obtained through the endoscope are totally different from those obtained through an abdominal opening or a laparoscope, and thus it is difficult to accurately detect an incision region outside the body. For this reason, incision accuracy and range have no choice but to vary depending on sensation, skill, etc. of a surgeon.

To solve this problem, bio-clips are disclosed in Korean Patent Application Publication No. 2005-0110013 titled "Clip and Clipping Instrument for Biological Tissues," U.S. Pat. No. 7,357,805 titled "Clip Device for Endoscope and Clip for Use Therein," etc., developed to stop bleeding during an endoscopic surgery. The disclosed bio-clips are installed in a separately manufactured clip manipulation device, and are transferred to a desired position inside a body to clip a biological tissue, thereby marking a position of the tissue to be incised.

However, once the bio-clip is clipped to the operation region inside the body, the surgeon cannot look at the bio-clip. Although the laparoscopic surgery has recently increased, it is impossible to directly touch a bio-clip, so that it is difficult to detect an accurate position of the incision region during the operation. Consequently, operation accuracy deteriorates, and the danger of side effects caused by excessive incision is considerable.

SUMMARY

The present embodiments are directed to providing a fluorescent indication clip for surgery that reinforces a function as a position indicator by mounting a photo-reactive fluorescent material on a bio-clip, allows a surgeon to rapidly and easily detect the accurate position of an internal operation region, and thus makes it possible to improve operation accuracy and reduce side effects caused by excessive incision.

These embodiments are not limited to the above-mentioned purpose, and other purposes will be clearly understood by those of ordinary skill in the art from the following description.

In example embodiments, a fluorescent indication clip for surgery includes: an automatically opening clip body; a fluorescent indicator prepared at a rear end of the clip body and including a photo-reactive fluorescent material; and a clamper configured to slide from a position at which the clamper is mounted on the fluorescent indicator to the clip body by an external force, and fasten the clip body to close front ends of the clip body.

The clip body may include: a base configured to be combined with the fluorescent indicator; two arms configured to extend from the base to the front; and spacers formed by bending front ends of the two arms inward, and configured to be clipped onto biological tissue.

Each of the two arms may include: a stop part on which a manipulation arm of a clip manipulation device is put; a step part formed at a rear end of the stop part to have a smaller plate width than the stop part, and configured to catch the stop part and keep the clip closed; and an automatically opening curved part formed to be concave between the step part and the base.

The stop part may be formed to be tapered from a front end to the rear end.

The clip body may be formed of a polymer mixed with a photo-reactive fluorescent material, or a photo-reactive fluorescent material may be coated on a surface of the clip body such that the clip itself fluoresces.

The fluorescent indicator may be detachably combined with the clip body, or formed in one body together with the clip body.

The fluorescent indicator may include: a case configured to contain the photo-reactive fluorescent material; and couplers prepared on the case to couple the case with the clip body.

The case may be formed of a transparent material and light-transmitting material.

The couplers may extend from two sides of a front end of the case to the front, coupling protrusions may be formed inward at respective ends of the extended couplers, and the rear end of the clip body may be inserted in the coupling protrusions and coupled to the couplers.

The clamper may include a clamping ring having a cylinder shape to be put on an external diameter of the fluorescent indicator and slide.

In other example embodiments, a fluorescent indication clip for surgery includes: a clip body; a fluorescent indicator formed in one body together with the clip body or detachably combined with a rear end of the clip body, and including a photo-reactive fluorescent material; and a clamping ring configured to slide from a position at which the clamping ring is mounted on the fluorescent indicator to the clip body and fasten the clip body by an external force such that the clip body can clip biological tissue.

Details on other example embodiments are included in the detailed description and drawings.

BRIEF DESCRIPTION OF THE DRAWINGS

The above and other objects, features and advantages of the present invention will become more apparent to those of ordinary skill in the art by describing in detail example embodiments thereof with reference to the attached drawings, in which.

DETAILED DESCRIPTION OF EXAMPLE EMBODIMENTS

Figure 1:
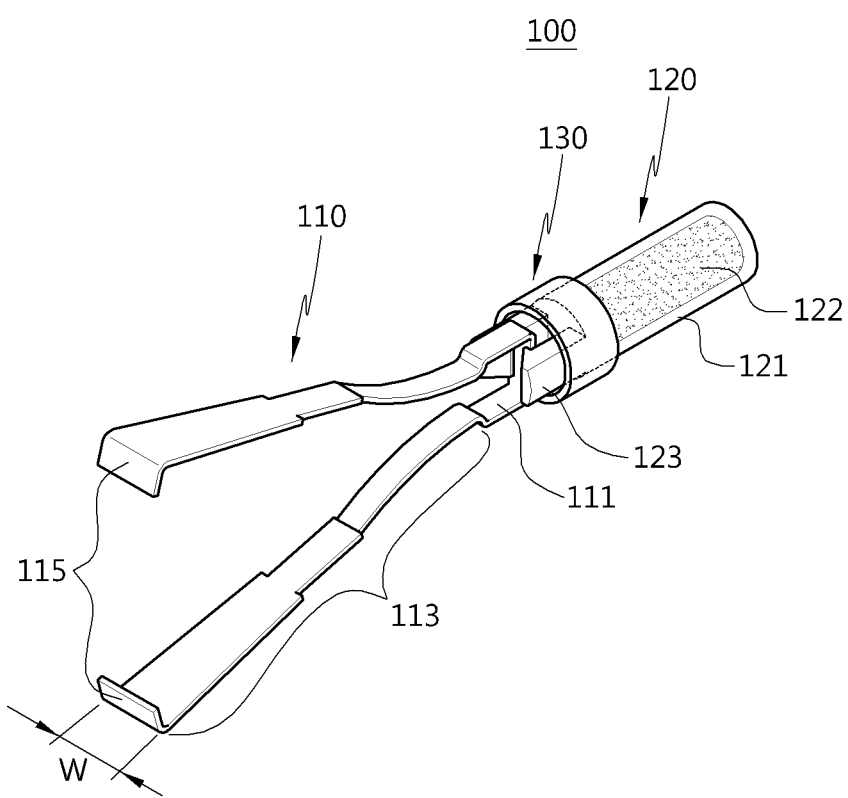
FIGS. 1 and 2 are perspective views of a fluorescent indication clip for surgery according to an example embodiment of the present invention.

Various example embodiments of the present invention will now be described more fully with reference to the accompanying drawings, in which some example embodiments of the invention are shown.

However, specific structural and functional details disclosed herein are merely representative, for purposes of describing example embodiments of the present invention. This invention may be embodied in many alternate forms and should not be construed as limited to only the embodiments set forth herein. Example embodiments of the invention are intended to cover all modifications, equivalents, and alternatives falling within the scope of the invention. Like numbers refer to like elements throughout the description and drawings.

It will be understood that, although the terms first, second, A, B, etc., may be used herein to describe various elements, these elements should not be limited by these terms. These terms are only used to distinguish one element from another.

For example, a first element could be termed a second element, and, similarly, a second element could be termed a first element, without departing from the scope of the example embodiments of the present invention. The term "and/or" is used herein to include any one of several items as well as any combination of some or all of the same items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to limit the present invention. Although some elements are referred to in the singular using the articles "a," "an" and "the," there may be more than one of them and the language used herein is not intended to limit their number. It will be further understood that the terms "comprises," "comprising," "includes" and "including" when used herein, specify the presence of stated features, numbers, steps, operations, elements and/or components, but do not preclude the presence or addition of one or more other features, numbers, steps, operations, elements, components and/or groups thereof.

Unless explicit definitions are given, all terms used herein, including technical and scientific terms, have the same meaning as commonly understood by those of ordinary skill in the art to which the invention pertains. Terms defined in a common dictionary are to be interpreted within the context of the relevant field, and are not to be interpreted as having idealized or excessively formal meanings unless explicit definition is given herein.

Among the terms used herein, a "leading end side" indicates a side in which biological tissue is present, and a "trailing end side" indicates the opposite side to the biological tissue.

Hereinafter, a fluorescent indication clip for surgery according to an example embodiment of the present invention will be described in detail with reference to the attached drawings.

Figure 2:
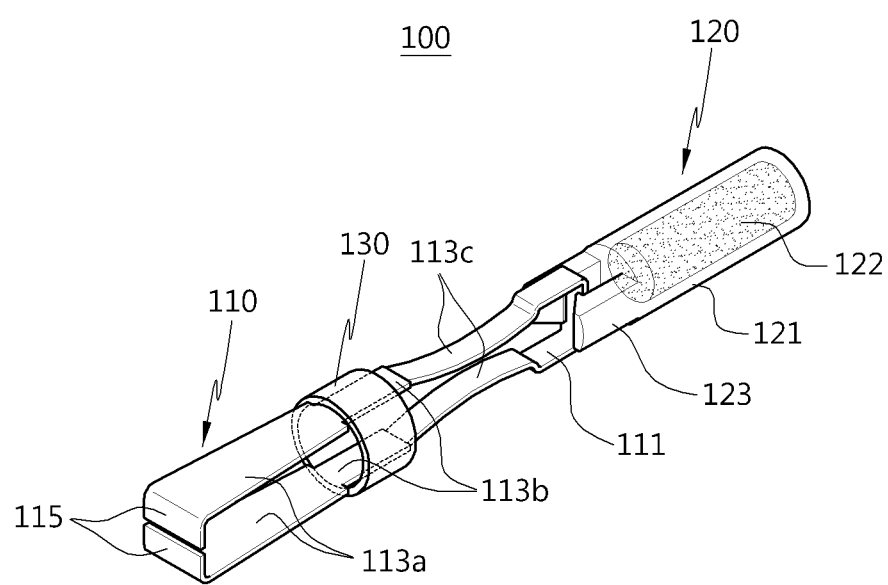
Figure 3:
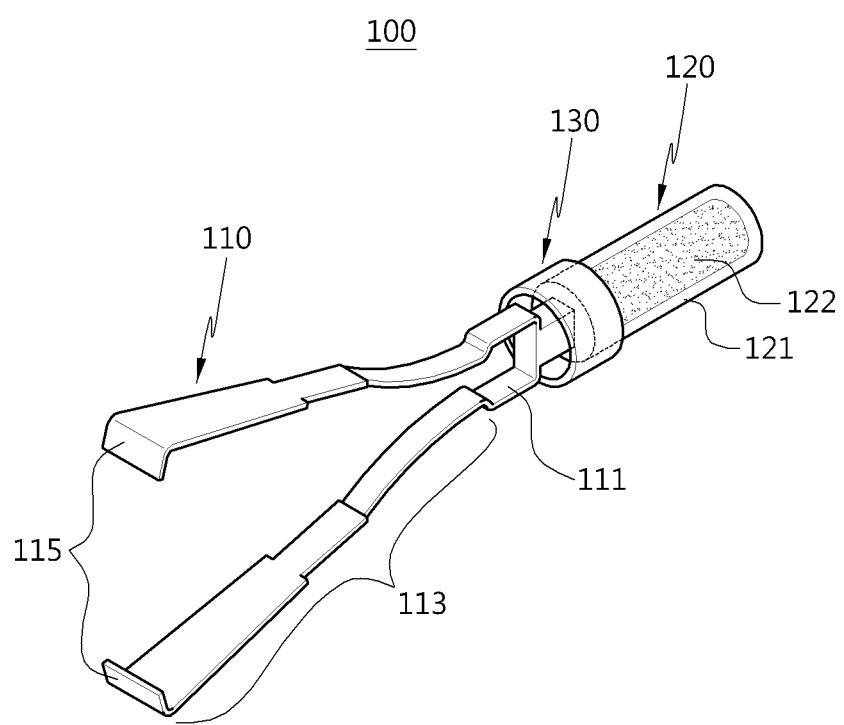
FIG. 3 is a perspective view of a fluorescent indication clip in which a clip body and a fluorescent indicator are formed in one body according to an example embodiment of the present invention.
Figure 4:
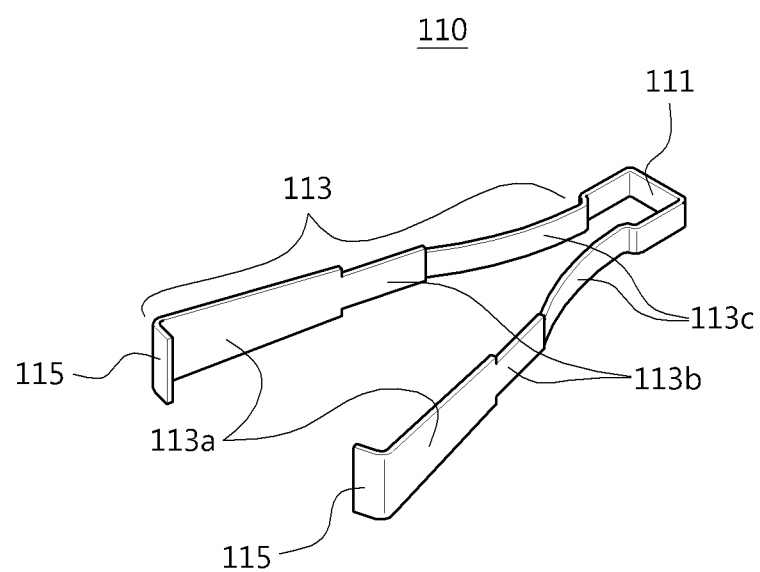
FIG. 4 is a perspective view of a clip body.
Figure 5:
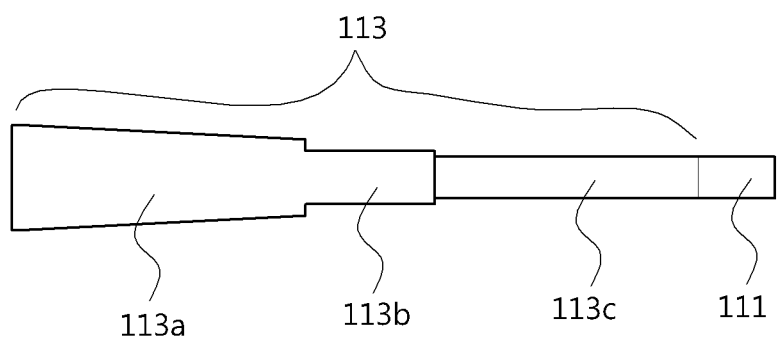
FIG. 5 is a side view of a clip body.
Figure 6:
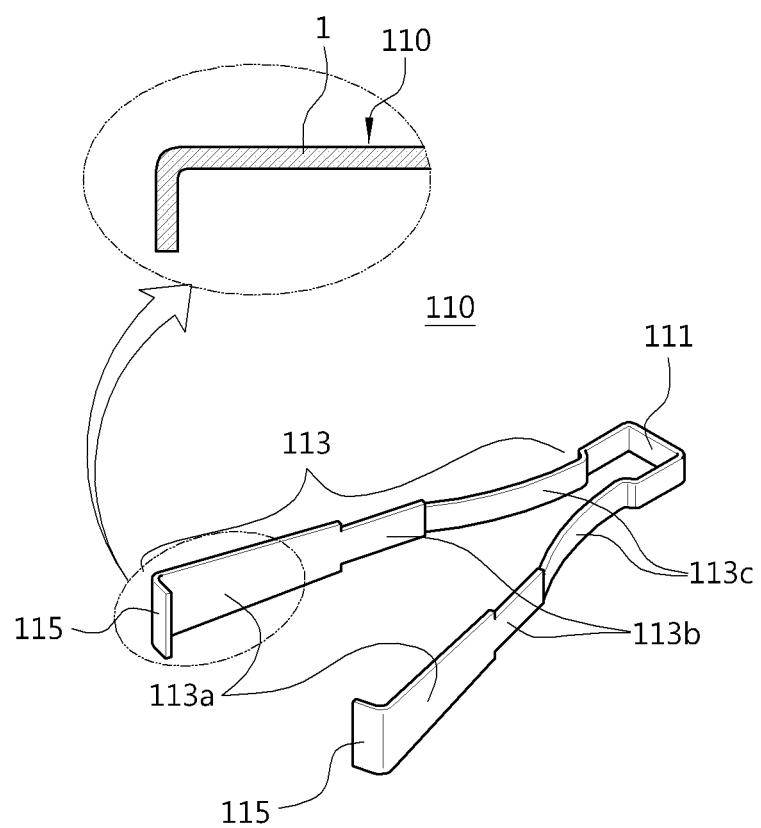
FIGS. 6 and 7 illustrate examples in which a fluorescent material is included in a clip body.
Figure 7:
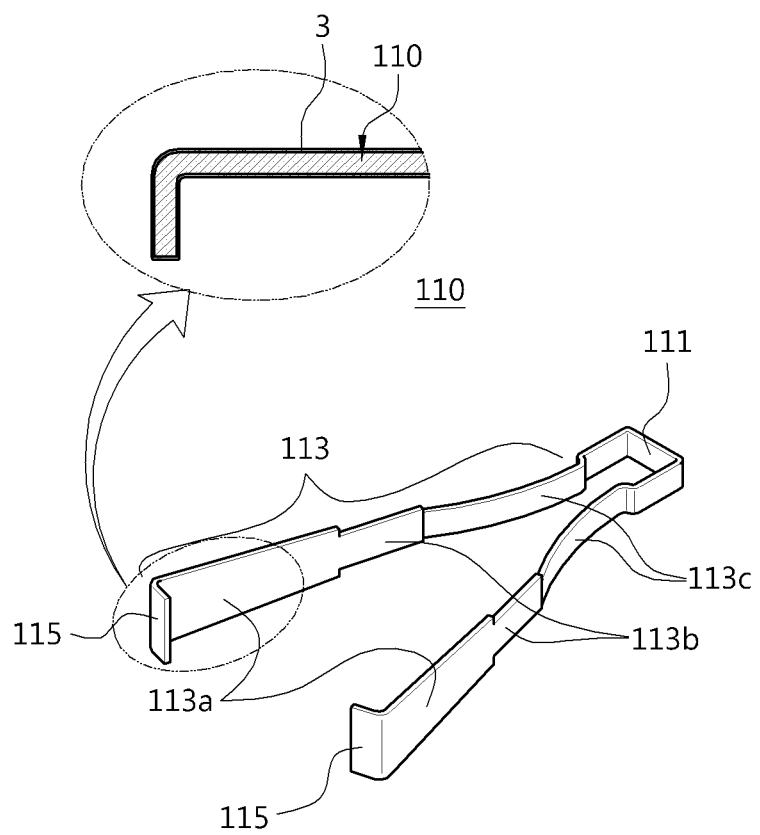
Figure 8:
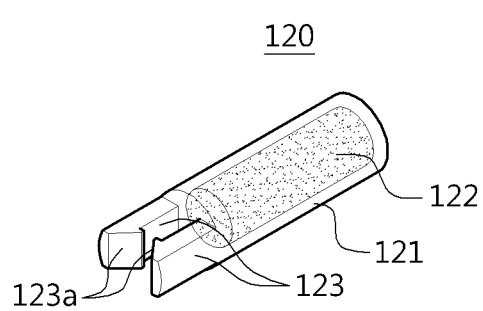
FIG. 8 is a perspective view of a fluorescent indicator.

FIGS. 1 and 2 are perspective views of a fluorescent indication clip for surgery according to an example embodiment of the present invention. FIG. 1 shows an open state of the clip, and FIG. 2 shows a closed state of the clip. FIG. 3 is a perspective view of a fluorescent indication clip in which a clip body and a fluorescent indicator are formed in one body, FIGS. 4 and 5 are a perspective view and a side view of a clip body, respectively, FIGS. 6 and 7 illustrate examples in which a fluorescent material is included in a clip body, and FIG. 8 is a perspective view of a fluorescent indicator.

As shown in FIGS. 1 to 8, a fluorescent indication clip 100 for surgery according to an example embodiment of the present invention may include a clip body 110, a fluorescent indicator 120, a clamper 130, and so on.

The clip body 110 may be manufactured by bending the middle of a thin and long metal plate spring. Here, since the metal plate spring constituting the clip body 110 is inserted in the cavity 11 of a clip manipulation device 10, which will be described later, to move forward and backward, a width w of the metal plate spring may be limited.

The clip body 110 has self-spreadability such that spacers 115, which will be described later, are open in a normal state in which no external force is applied.

The clip body 110 may be formed of a metal, such as stainless steel and a titanium alloy, or plastics, such as acrylonitrile-butadiene-styrene (ABS) resin, hard chlorinate vinyl resin, polyamide, and polyethylene, in order to prevent corrosion in the coelom, particularly in the stomach in which digestive enzymes are produced, etc. Also, the clip body 110 may be formed of a highly elastic material to open automatically in the normal state in which no external force is applied. Also, when the clip body 110 is formed of a polymer, a fluorescent material 1 may be mixed with the polymer during a process of manufacturing a polymer clip so that the polymer clip itself can fluoresce (see FIG. 6). Also, a thin coating layer 3 may be formed by coating a polymer including the fluorescent material 1 on the surface of the clip body 110 so that the clip can be manufactured to fluoresce (see FIG. 7).

The clip body 110 may include a base 111 and two arms 113 in addition to, the spacers 115.

In a use state of the fluorescent indication clip 100 (see FIGS. 9 and 10), the base 111 is on an opposite side to biological tissue (not shown), and is detachably coupled to coupling protrusions 123a of the fluorescent indicator 120 which will be described later.

In this example embodiment, the base 111 has a substantially "C"-shaped cross section. However, the base 111 is not limited to this shape, and any shape will do if the base 111 can be coupled to the coupling protrusions 123a of the fluorescent indicator 120.

The two arms 113 are formed to extend thin and long from two sides of the base 111 toward biological tissue, i.e., to the front.

Each of the two arms 113 may include a stop part 113a, a step part 113b, and a curved part 113c. The front end of a manipulation arm (or a manipulation wire) of the biological clip manipulation device 10, which will be described later, is stopped by the stop part 113a. The step part 113b is formed at a rear end of the stop part 113a to have a smaller plate width than the stop part 113a, and keeps the clip fixed and closed when the clamping ring 130, which will be described later, is caught by the step part 113b. The curved part 113c is formed to be concave between the stop part 113a and the step part 113b, and opens automatically. Here, the stop part 113a may be formed to be tapered from a front end to a rear end with a gradually reduced plate width, and have a structure that can be easily coupled to and separated from a manipulation arm 13, which will be described later.

The spacers 115 are formed by bending the front ends of the two arms 113 inward to clip biological tissue.

The base 111, the two arms 113, and the spacers 115 constituting the clip body 110 are not limited to the shape described in this example embodiment, but may be manufactured in various shapes. In other words, any automatically opening structure capable of clipping biological tissue may be used.

The fluorescent indicator 120 is prepared at the rear end of the clip body 110. The fluorescent indicator 120 may be detachably combined with the clip body 110 as shown in FIGS. 1 and 2, or formed in one body together with the clip body 110 as shown in FIG. 3.

The fluorescent indicator 120 may include a case 121, couplers 123, and so on.

The case 121 has a storage space of a predetermined size therein, and is sealed by a hermetic cover (not shown) after a photo-reactive fluorescent material 122 is stored in the storage space. Here, the photo-reactive fluorescent material 122 is a material that spontaneously emits light when light is radiated from a light source of a specific wavelength band, for example, a laser or light emitting diode (LED) harmless to a human body. The photo-reactive fluorescent material 122 may include a variety of fluorescent materials such as quantum dots having a core of nano-semiconductor particles (CdSe, CdTe, CdS, InAs, etc.), cyanine-based fluorescent dyes (Cy3, Cy5, Cy5.5, Cy7, etc.), and BODIPY-based fluorescent dyes (BODIPY 639/650-X STP ester). In particular, a fluorescent material that fluoresces in a near infrared wavelength band of 600 to 900 nm in response to radiated light may be efficiently used to fluoresce through thick biological tissue, and thus is useful in the present invention. Also, the photo-reactive fluorescent material 122 may be a solid or liquid type, and preferably is a liquid type.

Since the photo-reactive fluorescent material 122 generally includes ingredients harmful to a human body, the case 121 must have airtightness. Also, the case 121 may be formed of a transparent and light-transmitting material such as glass or plastic such that light emitted from an external light source is transmitted as much as possible and radiated onto the internal photo-reactive fluorescent material 122.

The couplers 123 are prepared at the case 121 such that the case 121 containing the photo-reactive fluorescent material 122 can be coupled to the clip body 110.

The couplers 123 extend from two sides of the front end of the case 121 to the front, and the coupling protrusions 123a are formed inward at the ends of the extended couplers 123. The base 111 of the clip body 110 is inserted into the coupling protrusions 123a so that the clip body 110 can be coupled to the couplers 123. Here, the front ends of the coupling protrusions 123a may be formed to incline inward and the rear ends of the coupling protrusions 123a may be formed vertically in order to facilitate coupling between the couplers 123 of the case 121 and the base 111 of the clip body 110 and prevent the coupled case 121 from being separated from the clip body 110. In this example embodiment, the couplers 123 have the coupling protrusions 123a, but various coupling structures may be used. For example, a female screw (not shown) may be formed in the base 111 of the clip body 110, and a male screw (not shown) may be formed at the front end of the case 121 so that the female and male screws can be engaged.

The clamper 130 slides from a position at which the clamper 130 is mounted on the fluorescent indicator 120 to the clip body 110 by an external force applied by the clip manipulation device 10 and narrows the spacers 115 of the clip body 110 to close so that the clip body 110 can clip the biological tissue.

The clamper 130 may be a cylindrical clamping ring that is slidably fitted around the outer circumference of the case 121 of the fluorescent indicator 120 and slide.

To apply an external force to the clamping ring 130 such that the clamping ring 130 slides from a mounted position of the fluorescent indicator 120 to the clip body 110, is caught and stably maintained by the step parts 113b, the clamping ring 130 may have an internal diameter that is larger than the external diameter of the case 121 of the fluorescent indicator 120 and the plate widths of the base 111, the step parts 113b, and the curved parts 113c and smaller than the plate width of the stop parts 113a of the clip body 110. Also, the clamping ring 130 may have a length corresponding to the length of the step parts 113b of the clip body 110.

A material for the clamping ring 130 is not substantially limited, but it may be formed of the same material as the clip body 110 because the clamping ring 130 is used together with the clip body 110. For example, the clamping ring 130 may be formed of a metal, such as stainless steel and a titanium alloy, or plastics, such as ABS resin, hard chlorinate vinyl resin, polyamide, and polyethylene.

Figure 9:
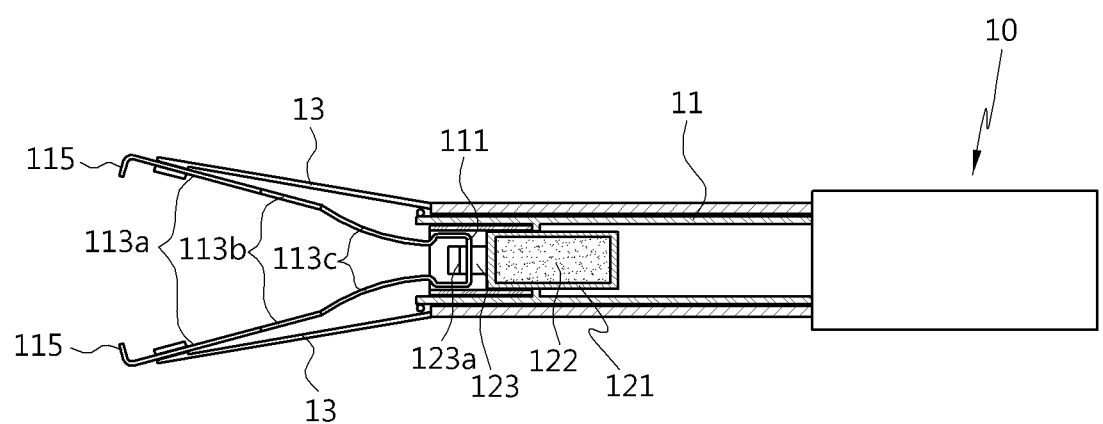
FIGS. 9 and 10 are cross-sectional views illustrating states of a fluorescent indication clip according to an example embodiment of the present invention.
Figure 10:
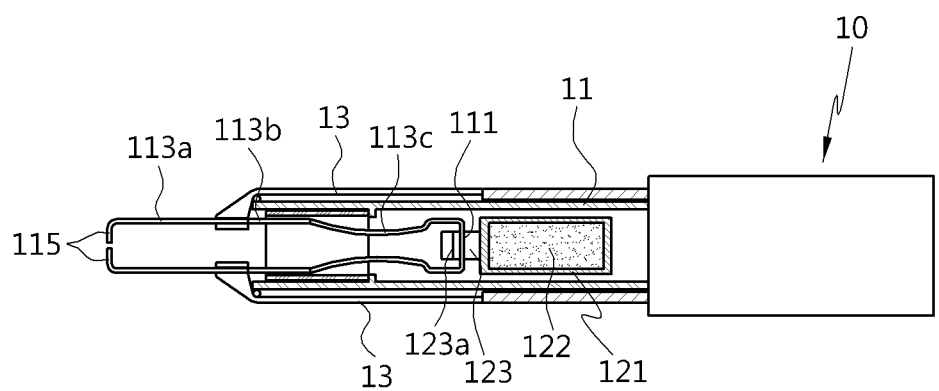

FIGS. 9 and 10 are cross-sectional views illustrating states of a fluorescent indication clip according to an example embodiment of the present invention. FIG. 9 is a cross-sectional view illustrating a state of the fluorescent indication clip installed on a clip manipulation device, and FIG. 10 is a cross-sectional view illustrating a fixed and fastening state of the fluorescent indication clip.

First, as shown in FIG. 9, the fluorescent indication clip 100 according to an example embodiment of the present invention is installed at the front end of the separately-manufactured clip manipulation device 10 to be used. For example, the stop parts 113a of the fluorescent indication clip 100 are put on the front ends of the manipulation arms 13 of the clip manipulation device 10, and the base 111 of the fluorescent indication clip 100 and the fluorescent indicator 120 are inserted into a cavity 11 of the clip manipulation device 10 to move forward and backward. Here, the clip manipulation device 10 is used to move the fluorescent indication clip 100 containing the photo-reactive fluorescent material 122 to a target region in a patient's internal organ, and fix the fluorescent indication clip 100 to the target region. The clip manipulation device 10 can be understood from the well-known art, and thus its detailed description will be omitted.

Subsequently, as shown in FIG. 10, the fluorescent indication clip 100 installed at the front end of the clip manipulation device 10 is moved to a target region in an internal organ, such as a colon or a stomach. When the fluorescent indication clip 100 arrives at the target region by the clip manipulation device 10, the manipulation arms 13 of the clip manipulation device 10 are pulled backward to close the stop parts 113a of the fluorescent indication clip 100, thereby fixing the fluorescent indication clip 100 to the target region. By pulling the manipulation arm 13, the two arms 113 of the clip body 110 are gradually inserted into the internal diameter of the clamping ring 130, beginning with the side of the base 111. When the clamping ring 130 is inserted into the step parts 113b of the clip body 110, the clamping ring 130 is caught and stopped by the step parts 113b, and the spacers 115 of the clip body 110 are narrowed and clipped onto biological tissue (not shown). At this time, since the clamping ring 130 is caught and securely fixed by the step parts 113b, the clip body 110 in the closed state can remain clipped onto the biological tissue for a long time regardless of the size of the biological tissue to be clipped.

Finally, when fixing and fastening of the fluorescent indication clip 100 is completed, the manipulation arm 13 is separated from the stop parts 113a, and the clip manipulation device 10 is pulled out of the body, thereby leaving only the fluorescent indication clip 100 containing the photo-reactive fluorescent material 122 at the target region in the internal organ.

As described above, when the fluorescent indication clip 100 containing the photo-reactive fluorescent material 122 is coupled to the rear end of the clip body 110, the fluorescent indication clip 100 is fixed in an operation region by clipping the region, and then light of a light source (not shown) having a specific wavelength band is radiated from outside, the photo-reactive fluorescent material 122 fluoresces, and thus the accurate position of the fluorescent indication clip 100 in a body can be easily and rapidly detected.

Thus, when the fluorescent indication clip 100 according to an example embodiment of the present invention is used, an incision region can be minimized in a colon cancer operation, a stomach cancer operation, and so on. That is, it is possible to improve operation effects and reduce side effects caused by excessive incision. Also, the fluorescent indication clip 100 according to an example embodiment of the present invention can be widely used as a position indicator that enables people to easily and rapidly detect a desired operation region in a stomach cancer operation, a colon cancer operation, and various surgical operations. Also, since a light source that is harmless to a human body, such as a laser or LED, is used to detect the position of the photo-reactive fluorescent material 122 added to the clip body 110, the fluorescent indication clip 100 has almost no effect on a patient in a operation and can be used in an existing laparoscopy by reducing the size of the clip manipulation device 10 and a light source (not shown).

A fluorescent indication clip for surgery according to example embodiments can improve a function as a position indicator by adding a photo-reactive fluorescent material to an existing bio-clip, and enables a surgeon to rapidly and easily detect the accurate position of an incision region during an operation. Thus, it is possible to improve operation accuracy and reduce side effects caused by excessive incision.

Also, since clip movement and coupling can be performed in a body using an existing endoscope as is, the clip can be used without additional video equipment in a operation.

Also, a light source that is harmless to a human body, such as a laser or LED, is used to detect the position of a fluorescent material added to a clip body, and thus a patient is scarcely affected during the operation, that is, a safe operation is enabled.

Also, when a light source is manufactured in a thin and long shape to pass through a trocar using an optical fiber, the clip can be used for laparoscopic surgery as well as abdominal surgery. The clip can be widely used as a position indicator that enables people to easily and rapidly detect a desired operation region in a stomach cancer operation, a colon cancer operation, and other various surgical operations.

Also, to effectively detect light emitted from a photo-reactive fluorescent material, a flat optical filter can be installed at the front end of an optical fiber, a surgical operator can be equipped with an optical filter in the form of glasses, or an optical filter can be installed on an optical transmission path inside an endoscope. Thus, it is possible to provide a new operation technique of performing an incision operation while checking the position of the clip through an endoscope screen visually.

The present invention is not limited to the above-described effects, and other effects which are not described above may be clearly understood by those of ordinary skill in the art from the claims.

While the invention has been shown and described with reference to certain example embodiments thereof, it will be understood by those skilled in the art that various changes in form and details may be made therein without departing from the spirit and scope of the invention as defined by the appended claims.

What is claimed is:

1. A fluorescent indication clip for surgery, comprising:
a clip body configured to expand automatically, comprising a base and two arms, wherein each arm comprises a spacer;
a fluorescent indicator located at the base of the clip body and comprising a photo-reactive fluorescent material and a case; and
a clamper configured to slide from a position at which the clamper is mounted on the fluorescent indicator to the clip body by an external force, and fasten the clip body to close the spacers of the clip body;
wherein the base is configured to be coupled to the fluorescent indicator;
the spacers are configured to clip biological tissue;
the case comprises a light-transmitting material and has a storage space configured to contain the photo-reactive fluorescent material therein, and the case comprises couplers configured for mounting the case to the base of the clip body;
the clip body contacts the coupling protrusions and the clip body is coupled to the case.

2. The fluorescent indication clip of claim 1, wherein the spacers comprise the front ends of the two arms, bent inward.

3. The fluorescent indication clip of claim 2, wherein each of the two arms includes:
a stop part, wherein each stop part comprises a spacer at one end;
a step part located at an end of the stop part opposite the spacer and having a smaller plate width than the stop part, and configured to catch the clamper and keep the clip narrow; and
a curved part configured to expand automatically and formed to be concave between the step part and the base.

4. The fluorescent indication clip of claim 3, wherein the stop part is tapered from the end at the spacer to the end at the step part.

5. The fluorescent indication clip of claim 1, wherein the fluorescent indicator is detachably coupled to the clip body.

6. The fluorescent indication clip of claim 1, wherein the fluorescent indicator and the clip body are configured to be attached with each other.

7. The fluorescent indication clip of claim 1, wherein the couplers extend away from the case from two sides of one end of the case, coupling protrusions extend inward at respective ends of the extended couplers, and the base of the clip body is inserted into the coupling protrusions.

8. The fluorescent indication clip of claim 1, wherein the clamper includes a clamping ring having a cylinder shape configured to slide along an external longitudinal surface of the fluorescent indicator.

* * * * *